(12) United States Patent
Daniel et al.

(10) Patent No.: US 9,877,817 B2
(45) Date of Patent: Jan. 30, 2018

(54) SURGICAL TOOL AND SYSTEM ADAPTED TO PLACE A CUFF OF AN ARTIFICIAL URINARY SPHINCTER AROUND A PORTION OF A URETHRA

(71) Applicant: Coloplast A/S, Humlebaek (DK)

(72) Inventors: Geoffrey A. Daniel, Crystal, MN (US); Neal Poucher, North Oaks, MN (US)

(73) Assignee: Coloplast A/S, Humlebaek (DK)

( * ) Notice: Subject to any disclaimer, the term of this patent is extended or adjusted under 35 U.S.C. 154(b) by 551 days.

(21) Appl. No.: 14/284,407

(22) Filed: May 22, 2014

(65) Prior Publication Data

US 2015/0335412 A1 Nov. 26, 2015

(51) Int. Cl.
*A61F 2/00* (2006.01)
*A61B 17/04* (2006.01)
*A61B 17/062* (2006.01)
*A61B 17/00* (2006.01)
*A61B 17/06* (2006.01)
*A61B 17/30* (2006.01)

(52) U.S. Cl.
CPC ........ *A61F 2/0036* (2013.01); *A61B 17/0469* (2013.01); *A61B 17/062* (2013.01); *A61B 2017/00128* (2013.01); *A61B 2017/00398* (2013.01); *A61B 2017/00805* (2013.01); *A61B 2017/0608* (2013.01); *A61B 2017/06042* (2013.01); *A61B 2017/306* (2013.01); *A61F 2/004* (2013.01)

(58) Field of Classification Search
CPC .... A61F 2/0036; A61F 2/004; A61B 17/0469; A61B 17/062; A61B 2017/06042; A61B 2017/0608; A61B 2017/00398; A61B 2017/306; A61B 2017/00128; A61B 2017/00805
See application file for complete search history.

(56) References Cited

U.S. PATENT DOCUMENTS

| | | |
|---|---|---|
| 3,744,063 A | 7/1973 | McWhorter et al. |
| 4,063,548 A | 12/1977 | Klatt et al. |
| 4,191,196 A | 3/1980 | Bradley et al. |

(Continued)

FOREIGN PATENT DOCUMENTS

WO 2014019632 2/2014

OTHER PUBLICATIONS

AMS 800 Urinary Control System, Operating Room Manual, Mar. 2004.

*Primary Examiner* — Christine H Matthews
*Assistant Examiner* — Kaylee Wilson
(74) *Attorney, Agent, or Firm* — Coloplast Corp., Coloplast A/S; Nick Baumann

(57) ABSTRACT

A surgical tool adapted for placement of a cuff of an artificial urinary sphincter around a portion of a urethra includes a head attached to a handle. The head has a recess formed in a first end surface of the head and two pads. The recess is sized to receive an inferior portion of the urethra. A first pad is located on a first side of the recess, and a second pad is located on a second side of the recess and spaced a gap distance away from the first pad. A piercing mechanism is located in and movable out of one of the first pad or the second pad. The piercing mechanism is movable across the gap distance between the first pad and the second pad to form a channel in tissue superior to the urethra.

14 Claims, 15 Drawing Sheets

(56) References Cited

U.S. PATENT DOCUMENTS

| | | |
|---|---|---|
| 4,222,377 A | 9/1980 | Burton |
| 4,412,530 A | 11/1983 | Burton |
| 4,878,889 A | 11/1989 | Polyak |
| 4,909,785 A | 3/1990 | Burton et al. |
| 4,932,956 A | 6/1990 | Reddy et al. |
| 4,932,958 A | 6/1990 | Reddy et al. |
| 4,994,020 A | 2/1991 | Polyak |
| 5,078,720 A | 1/1992 | Burton et al. |
| 5,335,669 A | 8/1994 | Tihon et al. |
| 5,356,423 A | 10/1994 | Tihon et al. |
| 5,496,271 A | 3/1996 | Burton et al. |
| 5,499,994 A | 3/1996 | Tihon et al. |
| 5,518,504 A | 5/1996 | Polyak |
| 5,720,415 A | 2/1998 | Morningstar |
| 5,895,356 A | 4/1999 | Andrus et al. |
| 6,382,214 B1 | 5/2002 | Raz et al. |
| 6,460,262 B1 | 10/2002 | Cabak et al. |
| 6,558,315 B1 | 5/2003 | Kuyava |
| 6,612,977 B2 | 9/2003 | Staskin et al. |
| 6,616,653 B2 | 9/2003 | Beyar et al. |
| 6,652,450 B2 | 11/2003 | Neisz et al. |
| 6,802,807 B2 | 10/2004 | Anderson et al. |
| 6,971,986 B2 | 12/2005 | Staskin et al. |
| 7,015,253 B2 | 3/2006 | Escandon et al. |
| 7,048,682 B2 | 5/2006 | Neisz et al. |
| 7,083,568 B2 | 8/2006 | Neisz et al. |
| 7,267,645 B2 | 9/2007 | Anderson et al. |
| 7,291,104 B2 | 11/2007 | Neisz et al. |
| 7,315,762 B2 | 1/2008 | Mosher et al. |
| 2004/0015177 A1* | 1/2004 | Chu ............ A61B 17/0469 606/139 |
| 2004/0034369 A1 | 2/2004 | Sauer et al. |
| 2006/0069396 A1 | 3/2006 | Meade et al. |
| 2006/0111732 A1 | 5/2006 | Gibbens et al. |
| 2007/0173864 A1* | 7/2007 | Chu ............ A61B 17/0401 606/139 |
| 2007/0239175 A1 | 10/2007 | Stokes et al. |
| 2009/0024145 A1 | 1/2009 | Meade et al. |
| 2011/0152891 A1 | 6/2011 | McLawhorn et al. |
| 2014/0088621 A1 | 3/2014 | Krieger et al. |

\* cited by examiner

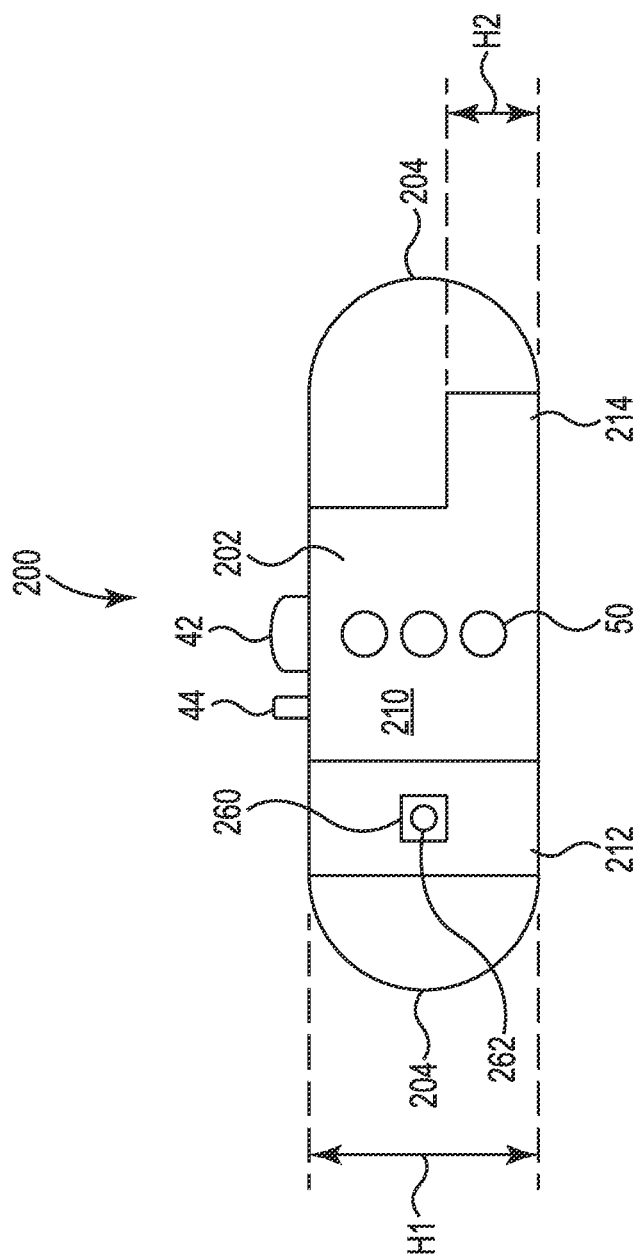

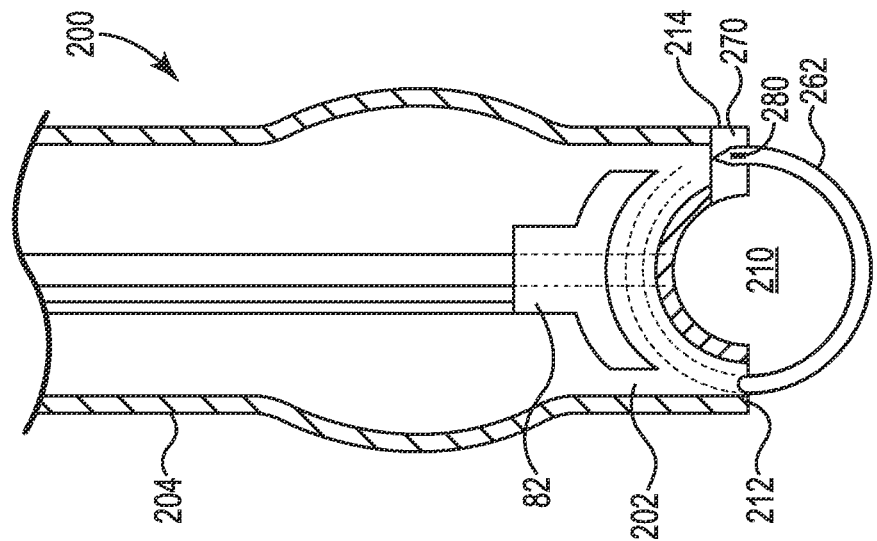
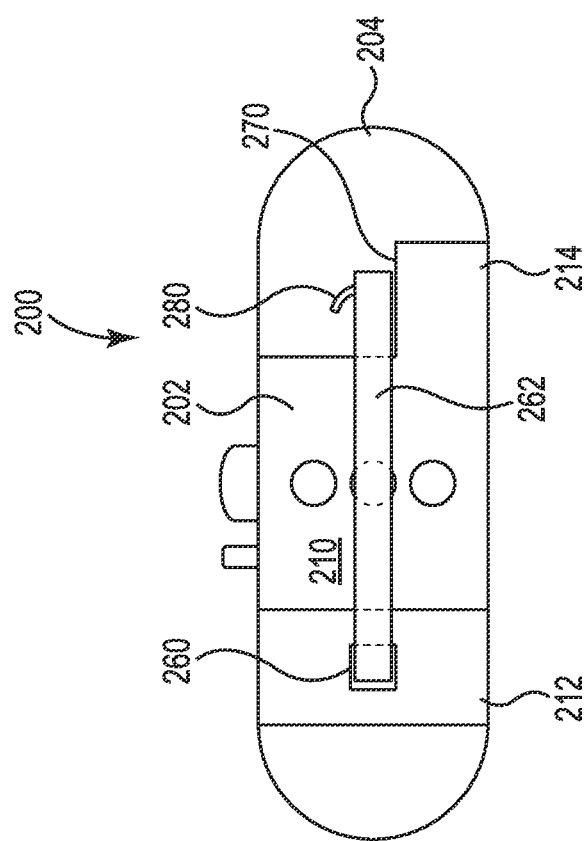

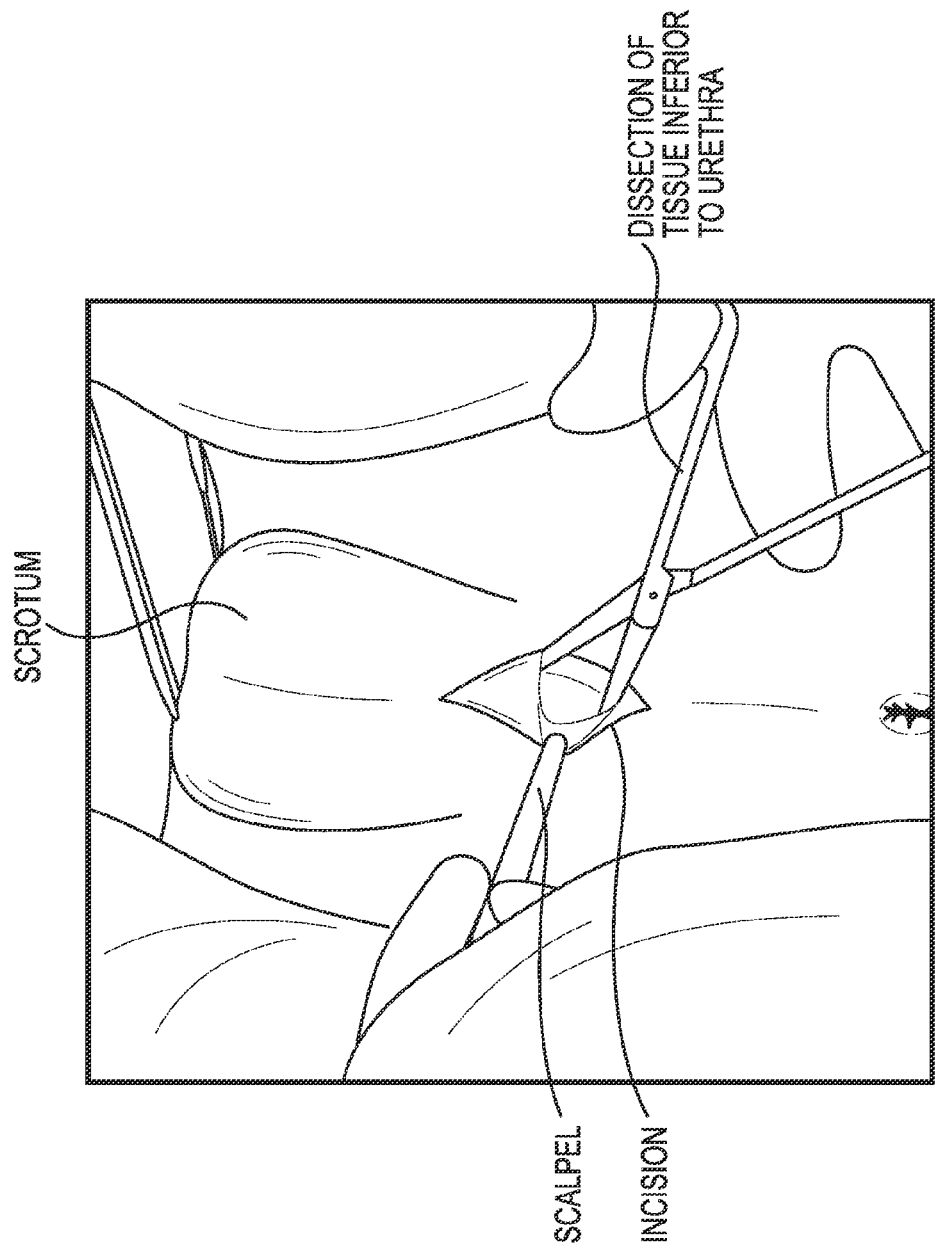

SURGICAL TOOL AND SYSTEM ADAPTED TO PLACE A CUFF OF AN ARTIFICIAL URINARY SPHINCTER AROUND A PORTION OF A URETHRA

BACKGROUND

Urinary incontinence affects about 200 million people worldwide and about 25 million people in the US. Urinary incontinence in women can be associated with a prolapse of one or more pelvic organs, which can arise from a weakness in the tissues/muscle of the pelvic floor. Urinary incontinence in men can arise after surgical treatment of the prostate glade, which treatment can include removal or weakening of the prostatic sphincter associated with the urinary urethra.

One treatment for urinary incontinence includes placing an artificial sphincter around a circumference of a portion of the urethra. The artificial sphincter operates to compress the urethra to selectively coapt or stop the flow of urine through the urethra, thus providing the user with a continent state. The artificial sphincter can be activated to an open position by the user, which opens the urethra and allows the user to selectively pass urine.

Surgeons and patients would welcome advances in the treatment of urinary incontinence.

SUMMARY

One aspect provides a surgical tool adapted for placement of a cuff of an artificial urinary sphincter around a portion of a urethra. The surgical tool includes a head attached to a handle. The head has a recess formed in a first end surface of the head and two pads. The recess is sized to receive an inferior portion of the urethra and is aligned with a central longitudinal axis of the handle. A first pad is located on a first side of the recess, and a second pad is located on a second side of the recess and spaced a gap distance away from the first pad. The first pad and the second pad are both located at a distal end of the tool. A piercing mechanism is located in and movable out of one of the first pad or the second pad. The piercing mechanism is movable across the gap distance between the first pad and the second pad to form a channel in tissue superior to the urethra, with the channel sized to receive the cuff of the artificial urinary sphincter.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 8 is a front end view of the surgical tool illustrated in FIG. 7.

FIG. 9A is a front end view of the tool illustrated in FIG. 7 showing a cutting blade of a piercing mechanism moved out of a head of the tool.

FIG. 9B is a cross-sectional view of the tool illustrated in FIG. 9A.

FIGS. 11-15 are schematic views of embodiments of the implantation of a cuff of an artificial urethral sphincter around a urethra of a patient assisted by the tool illustrated in FIG. 1.

DETAILED DESCRIPTION

Figure 1:
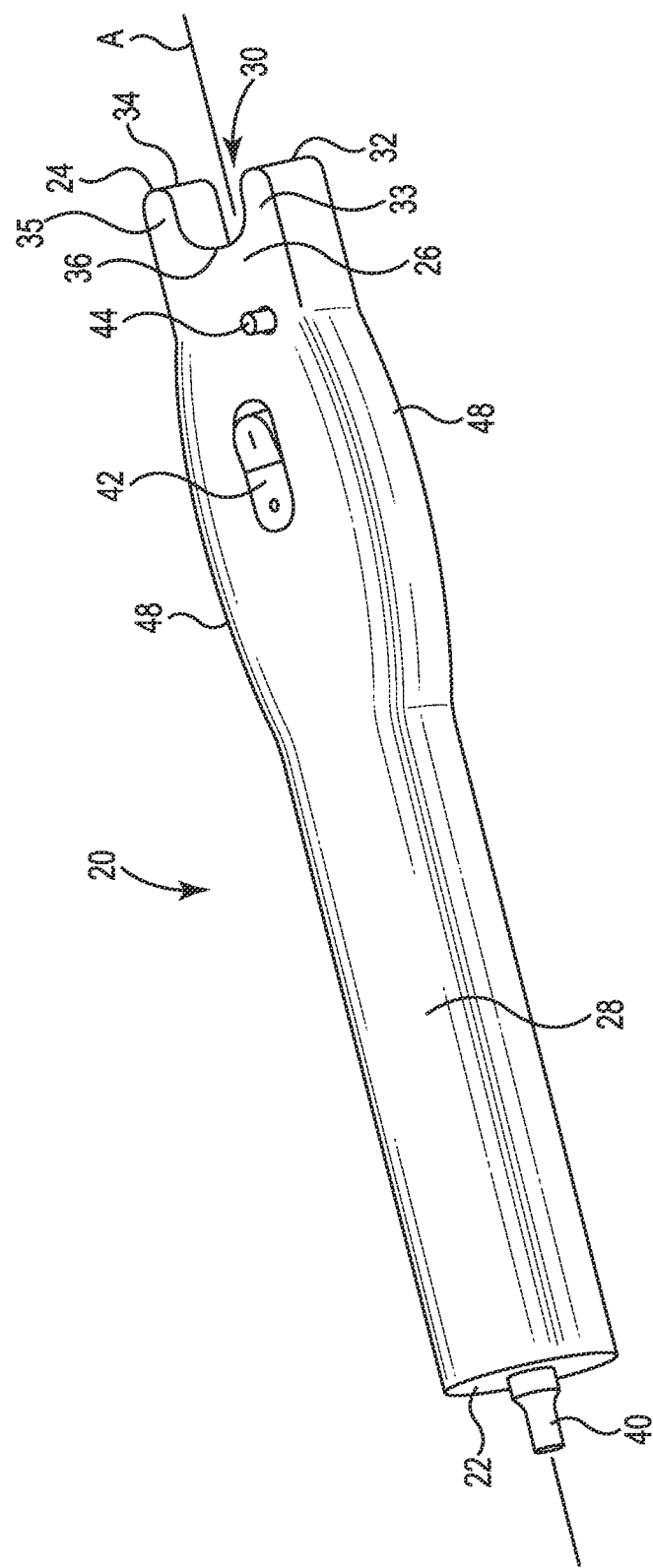
FIG. 1 is a perspective view of one embodiment of a surgical tool that is adapted for placement of a cuff of an artificial urinary sphincter around a portion of a urethra.

In the following Detailed Description, reference is made to the accompanying drawings that are a part of this application and illustrate various embodiments. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the invention. The following detailed description is not to be taken in a limiting sense, and the scope of the invention is defined by the appended claims.

The features of the various exemplary embodiments described in this application may be combined with each other ("mixed and matched"), unless specifically noted otherwise.

Soft tissue includes dermal tissue, sub-dermal tissue, ligaments, tendons, or membranes but does not include bone.

The term "superior" in this application is used to identify a location that is "behind" a reference surface. For example, the male urethra extends from the bladder to an exit in the glans penis. The urethra has one side portion that is nearest to the perineal skin (this is the inferior side of the urethra). The urethra has a second side portion that is father away from the perineal skin than the inferior side of the urethra, and the second side portion is termed the superior side of the urethra.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the prostate of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion from 1 inch to the first end and another end portion from 11 inches to the second end.

Immobilize means to prevent movement, for example in a manner by which a front face (or inferior portion) of the urethra is held in a still position.

Artificial urinary sphincters have proved useful in the treatment of urinary incontinence. An artificial urinary sphincter is implanted around the urethra and is operable to selectively coapt the lumen in the urethra to allow the user to shift the sphincter from an open State that allows urine to pass a closed State that provides the user with a continent State.

Implanting of the artificial urinary sphincter around the urethra includes dissecting tissue away from the urethra to form a path around the urethra that is sized for insertion of a cuff of the sphincter. The surgical procedure is typically performed with the patient in a lithotomy position with the patient on his/her back and the legs and an elevated position. Dissecting tissue away from the inferior side of the urethra is comparatively routine in the surgical sense for the reason that the surgeon has a complete, full field view of the inferior side of the urethra. Dissecting tissue away from the superior side of the urethra is challenging in that it involves dissecting tissue behind urethra that is out of the line of sight of the surgeon. Some part of this dissection is done by feel with the surgeon exercising deep caution to avoid nicking or cutting the urethra. Surgeons would welcome a tool or device that would assist in the dissection of tissue superior to the urethra.

Embodiments provide a tool that assists in the placement of a cuff of an artificial urinary sphincter around the urethra. The tool includes a recess that engages with or immobilizes the inferior portion of the urethra. The tool also includes a piercing mechanism that is configured to move in a calculated path to pierce tissue superior to the urethra as the interior side of the urethra is immobilized by the tool. One example of the tool provides for suction that pulls the inferior side of the urethra slightly in the distal direction to provide added clearance for the piercing mechanism to move superior to the urethra and form a pathway behind urethra.

Embodiments provide an all-in-one tool for forming a passage in tissue behind (superior) to the urethra and delivering the cuff of an artificial sphincter through the passage.

FIG. 1 is a perspective view of one embodiment of a tool 20 that is useful in placing a cuff of an artificial urinary sphincter around a urethra. The tool 20 is illustrated oriented on a longitudinal axis A extending from a proximal end 22 to a distal end 24. The tool 20 includes a head 26 attached to a handle 28. The handle 28 is sized to be held in one hand by the surgeon and the head 26 is sized for insertion into a perineal incision to engage with at least the inferior side of the urethra of the patient.

The head 26 includes a recess 30 that is formed in the distal end 24, with a first pad 32 located on an end of a first arm 33 on a first side of the recess 30 and a second pad 34 is located on an end of a second arm 35 on a second side of the recess 30. The recess 30 is sized to receive the inferior portion of the urethra. In one embodiment, the recess 30 is provided as a concave face 36 that is aligned on the central longitudinal axis A. The first pad 32 and the second pad 34 are both located at the distal end 24 of the tool 20 (which is to say, the pads 32, 34 are located at the distal-most end of the tool 20).

The face 36 is concave when viewed in a lateral (side-to-side) longitudinal cross-section (for example, when viewed from above). In the illustrated embodiment, the recess 30 has a flat or planar face from top-to-bottom (for example, when the recess 30 is viewed in a vertical longitudinal cross-section). Other surface smoothing or the application of blended radii on the face 36 is also acceptable.

The concave face 36 is provided with a curvature that is similar to (the curvature complements) a curvature of the inferior side of the urethra, which allows the recess 30 to form around the exposed inferior side of the urethra. In some embodiments, a surface of the recess 30 is provided with a suction mechanism that is configured to engage with and immobilize the urethra.

The handle 28 is oriented along the central longitudinal axis A and is provided with a connector 40 and an actuator including a first switch 42 and a second switch 44. In one embodiment, the connector 40 is a quick-connect connector attachable to an air or suction source provided in the surgical suite that is operable to deliver suction through the recess 30. The first switch 42 is provided to selectively initiate the suction and to selectively turn the suction off. The second switch 44 is provided to activate a piercing mechanism that operates to form a channel in the tissue superior to the urethra. In one embodiment, the connector 40 is located on the proximal end 22 of the tool 20 and has both an electrical conduit and a suction conduit provided through multiple ports that independently operate the suction function and the piercing function.

The handle 28 is sized for comfortable manipulation by the surgeon and includes a pair of opposing and gently curved bulbs 48 located in a region of the switches 42, 44. The bulbs 48 provide a level of lateral support that mitigates twisting as the distal end 24 of the tool 20 extends from the surgeon's hand. The handle is suitably fabricated from plastic and can include a pair (or more than two) snap-together portions that attach to provide a housing for the handle 28.

In one embodiment, the arms 33, 35 include measurement indicia extending from the pads 32, 34 back toward the handle 28 in increasing numerical size (e.g., from 0 mm to 15 mm as one example). The indicia are provided to indicate to the surgeon a depth into which the arms (or head 26) is inserted into a perineal incision or into the tissue on either side of the urethra.

Figure 2:
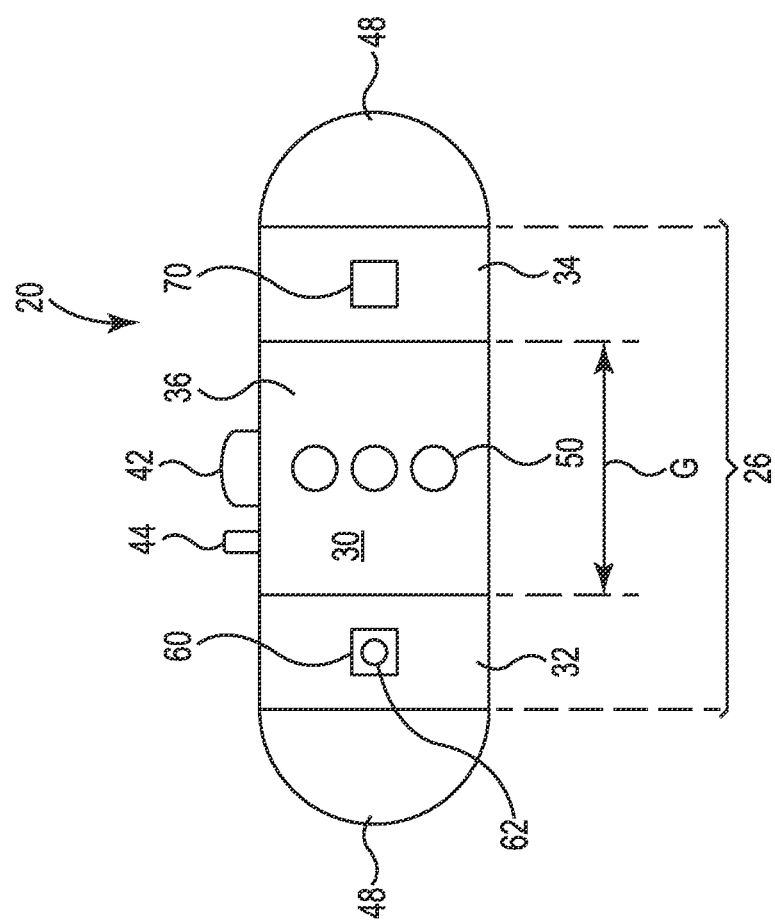
FIG. 2 is a front end view of the tool illustrated in FIG. 1.

FIG. 2 is a front end view of the head 26 of the tool 20.

In one embodiment, the recess 30 is provided with a suction port 50. In the illustrated embodiment, the suction port 50 is aligned on the central longitudinal axis A such that the suction port 50 is centered on the concave face 36 between the pads 32, 34. The embodiment of FIG. 2 illustrates three suction ports 50, although it is acceptable to provide more than three suction ports or fewer than three suction ports. For example, one useful embodiment includes a single suction port 50 shaped as an elongated oval oriented between the top surface and the bottom surface of the head 26.

In one embodiment, one of the ports 50 is provided with a digital camera that is electrically connected with an electrical conduit wired through the handle 28. The camera is provided to allow the surgeon to visualize engagement of the head 26 with the urethra.

The first pad 32 of the head is spaced a gap distance G from the second pad 34. The recess 30 extends between the first pad 32 and the second pad 34, and in one embodiment the recess 30 is a concave face that extends continuously between the pads 32, 34.

The head 26 is provided with a piercing mechanism that is operable to pierce tissue behind or superior to the urethra. In one embodiment, the first pad 32 includes an opening 60 that retains a piercing mechanism 62 and the second pad 34 has an opening 70 that is sized to receive the piercing mechanism 62. The piercing mechanism 62 is movable out of the first opening 60 across the gap distance G and into the second opening 70. This movement is calibrated to pierce the body tissue behind the urethra in a manner that obviates dissection of the tissue superior to the urethra. The gap distance G is selected to provide clearance of the recess 30 around the urethra and the muscle and connective tissue connected to the urethra. Suitable sizes for the gap distance G are in the range from 0.5 to 3.0 cm.

Figure 3:
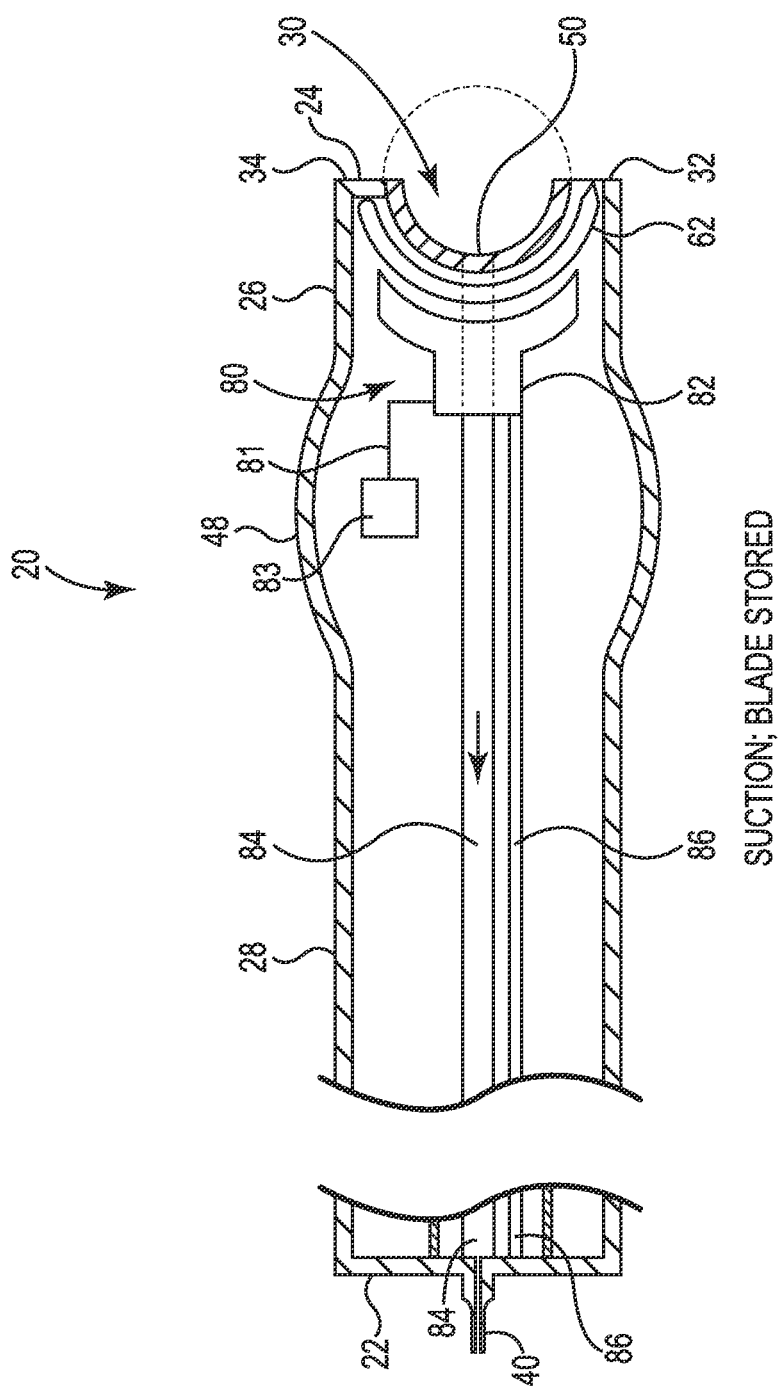
FIG. 3 is a cross-sectional view of the tool illustrated in FIG. 1 with a cutting blade of a piercing mechanism retained within a head of the tool.
Figure 4:
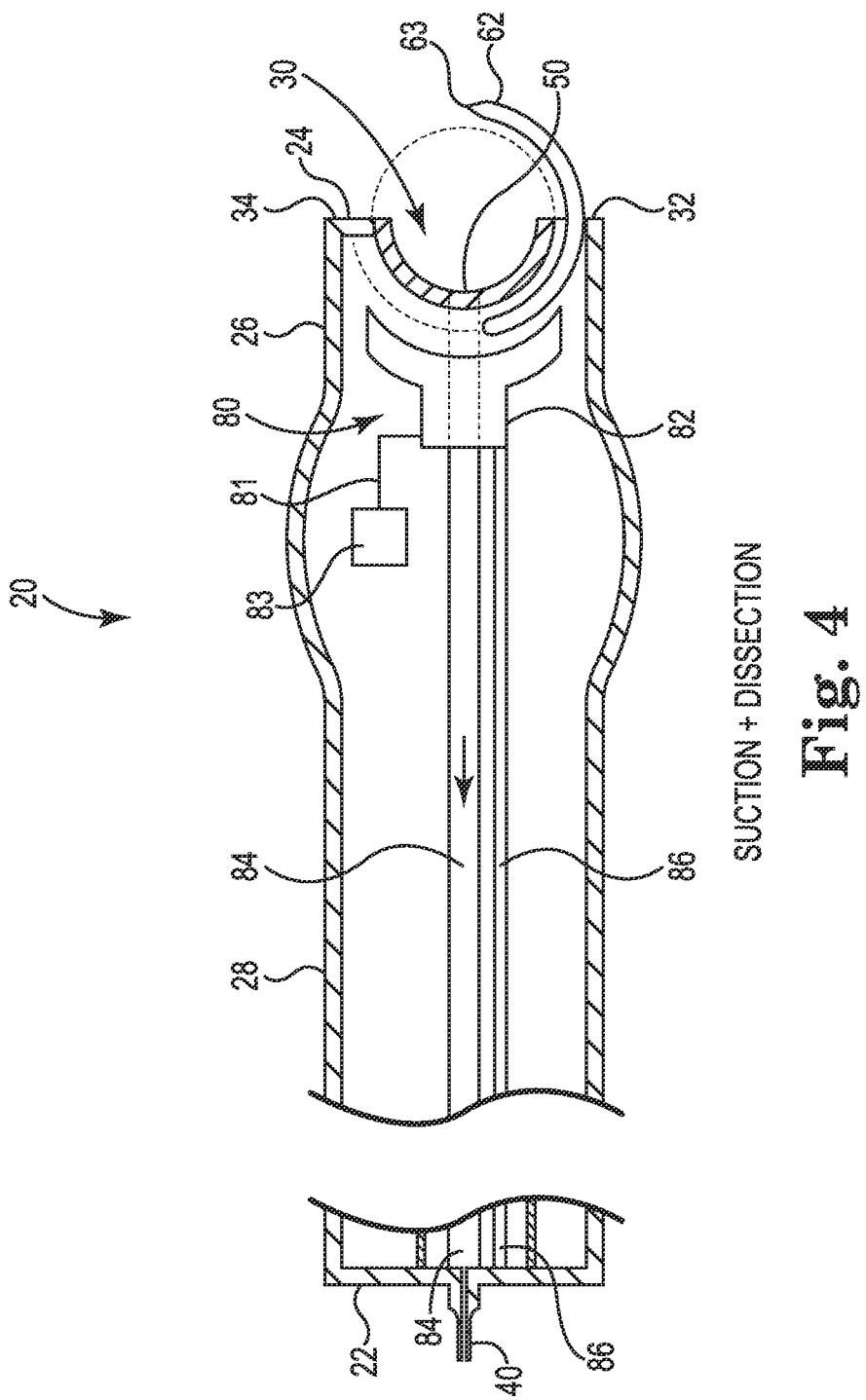
FIG. 4 is a cross-sectional view of the tool illustrated in FIG. 1 showing the cutting blade extended out of the head of the tool.
Figure 5:
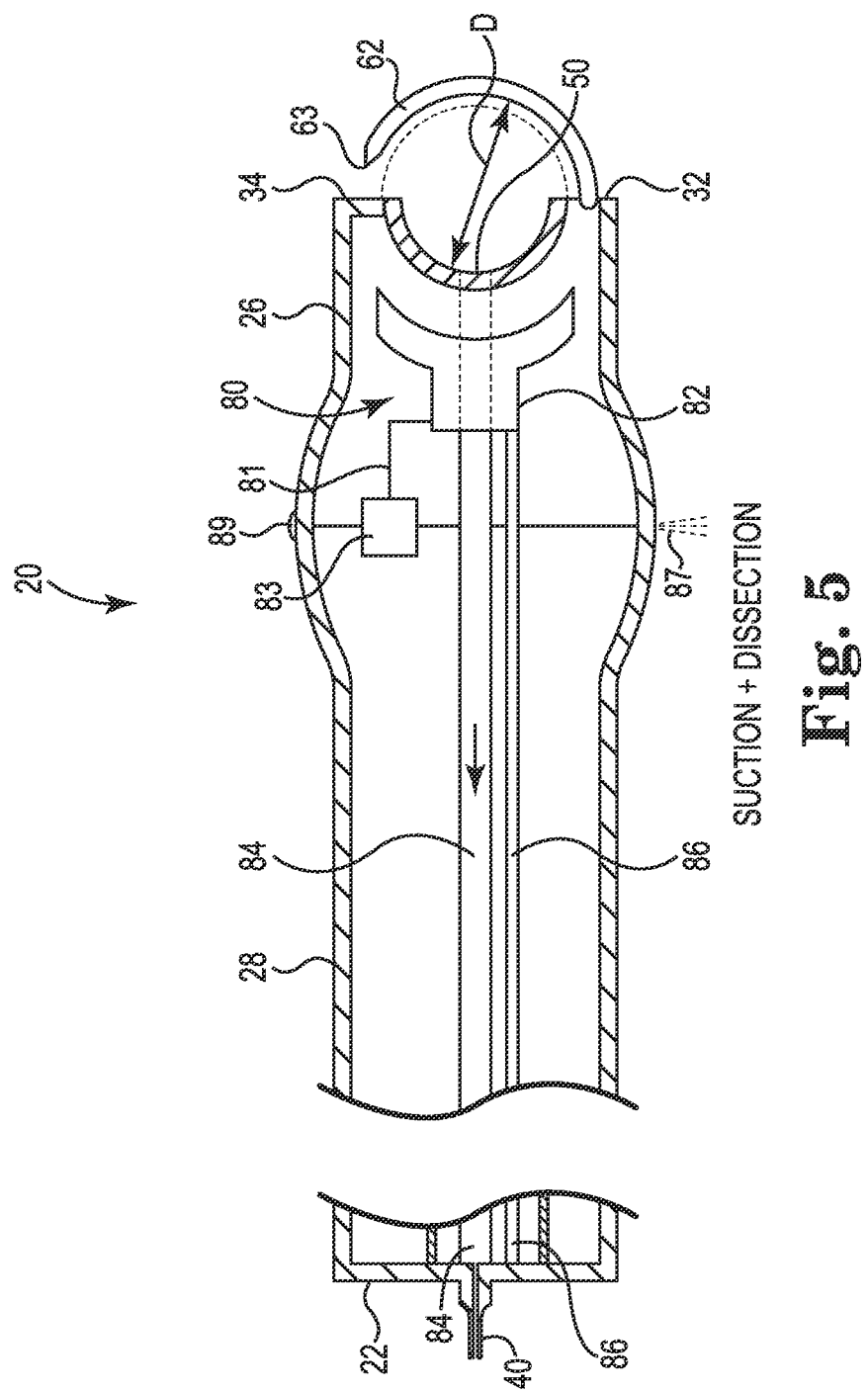
FIG. 5 is a cross-sectional view of the tool illustrated in FIG. 1 with the cutting blade deployed from the head of the tool.

FIG. 3, FIG. 4, and FIG. 5 are top cross-sectional views of the tool 20. The top lateral cross-section shows the curved bulb 48 in the handle 28 with the tool 20 extending between the proximal end 22 and the distal end 24.

The piercing mechanism 62 is associated with an actuator 82 and these components are retained within the head 26 and the handle 28. In one embodiment, the piercing mechanism 62 is formed in a semicircular arc (a half circle) and includes a sharp tip 63 adapted to pierce through tissue. The piercing mechanism 62 is suitably fabricated from metal, such as stainless steel.

The piercing mechanism 62 is pushed through the tissue, or activated, by the actuator 82. The actuator 82 is electrically connected at 81 with an integrated circuit 83 that is programmed/designed to logically control the piercing mechanism 62 and the switches 42, 44 and their operation. The actuator 82 includes pneumatic actuators, electric actuators, or mechanical actuators. For example, in one embodiment the connector 40 is configured to be coupled to a suction source provided in most surgical suites. The connector 40 communicates with the actuator 82 through one or more of a first conduit 84 and a second conduit 86.

In one embodiment, the first conduit 84 is a suction conduit that communicates between the suction port 50 formed in the recess 30 and the connector 40. The first switch 42 (FIG. 1) is operable between an on position in which suction is provided to the suction port 50 and an off position that returns the suction port 52 to ambient pressure. During use, the surgeon toggles or otherwise activates the first switch 42 to initiate suction through the suction port 50. The suction port 52 operates to immobilize the urethra when the tool 20 is placed in contact with the urethral tissue.

In one example, the actuator 82 is a pneumatic actuator. The pneumatic actuation of the actuator 82 operates to drive the piercing mechanism 62 with pressurized air provided through conduit 86. Suitable pneumatic actuators including miniaturized fittings and controllers are available from Pneumadyne, Plymouth, Minn. The piercing mechanism 62 is retained within a trace and the pneumatic actuator 82 is provided to drive the piercing mechanism 62 out of the first pad 32 and in a direction of the second pad 34. The piercing mechanism 62 is suitably provided with a biasing mechanism that returns the piercing mechanism 62 along its trace back from the second pad 34 into the first pad 32. Alternatively, the removal of the pressurized air source returns the piercing mechanism 62 from the second pad 34 back to the first pad 32

In one example, the actuator 82 is electrical actuator. Electrical actuation of the actuator 82 is energized by electrically connecting the piercing mechanism 62 within energy source communicating through the conduit 86. Suitable electric actuators including miniaturized controllers are available from EXLAR Corporation, Chanhassen, Minn. The energy source is suitably connected directly to the conduit 86 or through a multi-port provided in the connector 40. When energized, the piercing mechanism 62 is moved out of the first pad 32 and toward the second pad 34. The electrical current may be employed to return the cutting blade along its trace back into the head 26. Alternatively, a biasing mechanism is coupled to the piercing mechanism 62 and operates to return the piercing mechanism 62 to a storage position within the head 26.

In one embodiment, the piercing mechanism 62 is coupled to a mechanical linkage within the actuator 82. The mechanical linkage is suitably provided as a blade slider similar to the mechanism provided on a utility knife. The blade slider coupled with the piercing mechanism 62 provides direct 1-to-1 feedback to the surgeon correlating the movement of the piercing mechanism 62 to the manual movement of the blade slider. In one embodiment, the blade slider occupies the location of the second switch 44 (FIG. 1) and is located on a top surface of the tool 20.

FIG. 3 illustrates the tool 20 in a state suited for immobilizing the urethra. Suction is provided through the first conduit 84 to the suction port 50. The blade or piercing mechanism 62 is retained within the head 26 in a storage position.

FIG. 4 illustrates the tool 20 in a state suitable for immobilizing the urethra and dissecting tissue superior to the urethra by directing the piercing mechanism 62 in a semicircular arc out of the first pad 32.

FIG. 5 illustrates the tool 20 in a state suitable for immobilizing the urethra and forming a channel in a path extending entirely superior to the urethra. The piercing mechanism 62 has traversed behind the urethra in a path outward from the first pad 32 toward the second pad 34.

The recess 30 and the piercing mechanism 62 combined to provide a diameter D that is larger than the typical diameter of the bulbar urethra. As an example, after the inferior tissue is dissected, the exposed bulbar has a diameter of approximately 15 mm. The diameter D formed by the recess 30 and the piercing mechanism 62 is suitably sized in a range from 5 mm-30 mm, with one appropriate diameter being about 25 mm.

It is useful to provide the surgeon with feedback as to the location, position, and action of the piercing mechanism 62. In one embodiment, a visual indicator 87 is electrically connected to the integrated circuit 83 and operates to flash a light to indicate to the surgeon that the piercing mechanism 62 has been activated. In one embodiment, an aural indicator 89 is electrically connected to the integrated circuit 83 and operates to sound an audible tone to indicate to the surgeon that the piercing mechanism 62 has been activated. The visual indicator 87 and the aural indicator 89 are suitably programmed to provide output to the surgeon during the complete cycling of the piercing mechanism 62.

Figure 6:
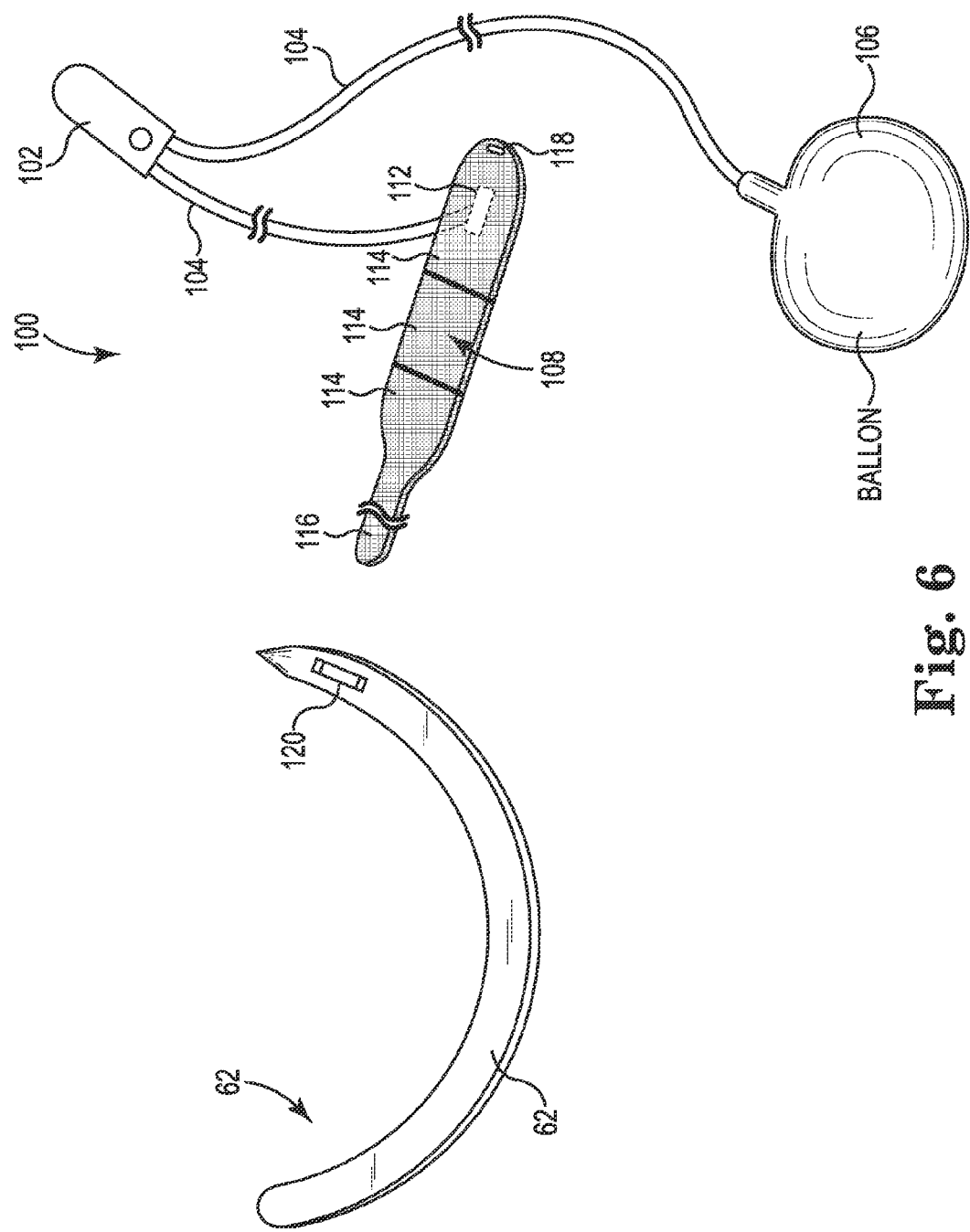
FIG. 6 is a perspective view of one embodiment of the cutting blade illustrated in FIG. 5 alongside an artificial urinary sphincter system.

FIG. 6 is a perspective view of the piercing mechanism 62 and an artificial urinary sphincter system 100. The piercing mechanism 62 is typically integrated into the tool 20 (FIG. 5) and is not removable from the head 26. However, the piercing mechanism 62 is shown isolated apart from the tool 20 to better illustrate features of the cutting blade 62 provided to deliver a portion of the artificial sphincter through the tissue channel formed by the blade 62.

The artificial urinary sphincter system 100 includes a pump 102 connected by tubing 104 to a pressurized reservoir 106 and a cuff 108. The pump 102 operates to move pressurized fluid from the reservoir 106 into the cuff 108, which inflates the cuff 108. The cuff 108 has a length sized for placement around the bulbar urethra, for example one suitable length for the cuff 108 is in a range from 4-10 cm.

Inflation of the cuff 108 by the pressurized liquid stored in the reservoir 106 is adapted to coapt the urethra when the system 100 is implanted in the patient. The pump 102 also operates to move fluid out of the cuff 108 and back into the reservoir 106 to deflate the cuff 108. The deflation of the cuff 108 is adapted to remove compression against the urethra, which allows the patient to pass urine.

The cuff 108 takes the form of a rectangular belt or strap that is sized to be engaged around the urethra of the patient. The cuff 108 includes a manifold 112 that is connected to the tubing 104 and inflatable pocket sections 114 that are in fluid communication with a manifold 112. The cuff 108 includes an attachment member 116 on one end of the cuff 108 that is sized for engagement with a fixation member 118 on an opposite end of the cuff 108. The cuff 108 is placed around the urethra by directing the attachment member 116 behind urethra and into engagement with the fixation member 118. Securing the attachment member 116 to the fixation member 118 attaches the cuff 108 around the urethra.

In one embodiment, the piercing mechanism 62 includes an engagement device 120 that is provided to grasp the attachment member 116 of the cuff and direct a portion of the cuff 108 around the superior section of the urethra as the piercing mechanism 62 forms a channel behind urethra. The engagement device 120 provides means for engaging with the cuff 108 of the artificial urinary sphincter system 100. These means for engagement with the cuff 108 include a slot that is sized to receive the attachment member 116, a clasp that operates to grasp the attachment member 116 of the cuff 108, and a projection that pierces through the material/fabric of the attachment member 116. The engagement device 120 configures the tool as an all-in-one tool for forming a passage in tissue behind (superior) to the urethra and delivering the cuff of an artificial sphincter through the passage.

Figure 7:
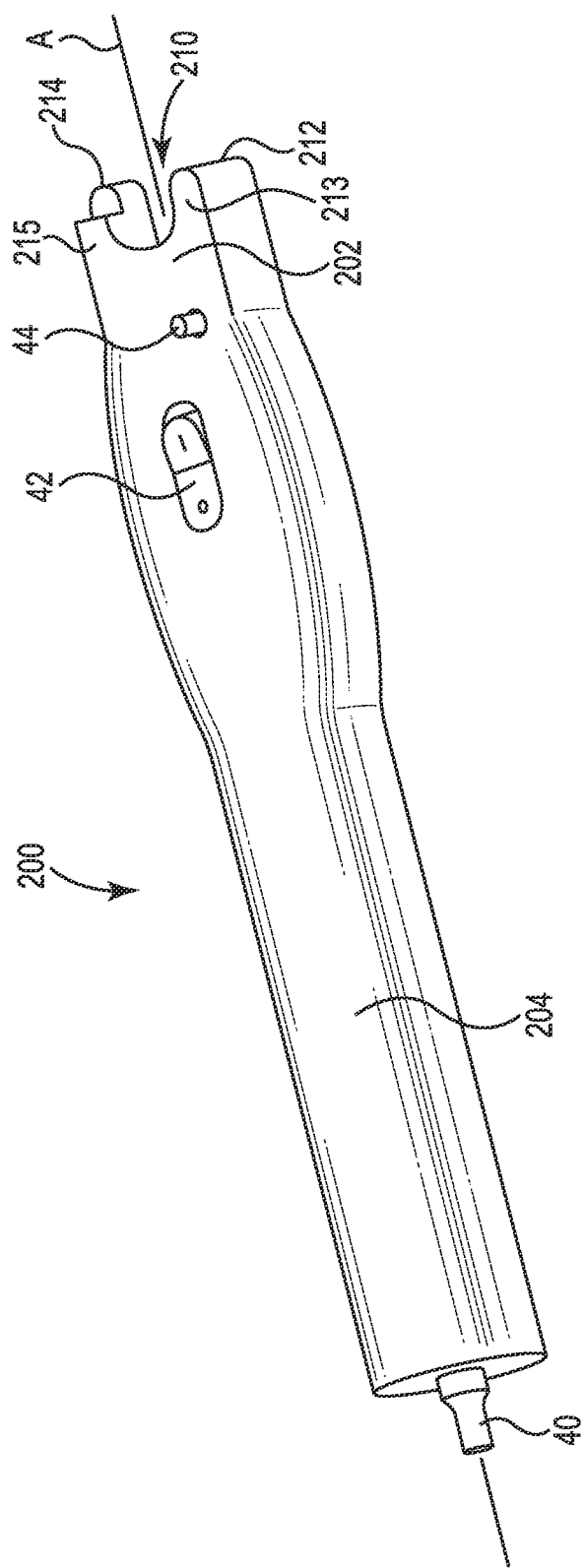
FIG. 7 is a perspective view of one embodiment of a surgical tool that is adapted for placement of a cuff of an artificial urinary sphincter around a portion of a urethra.

FIG. 7 is a perspective view of one embodiment of a surgical tool 200. The tool 200 includes a head 202 attached to a handle 204. The handle 204 is similar to the handle 28 described above and is sized to fit comfortably in the hand of the surgeon. The head 202 is constructed differently from the head 26 described above, but is also sized for insertion into a perineal incision to engage with at least the inferior side of the urethra of the patient.

The head 202 includes a recess 210 that is formed in the forward, distal end of the tool 200, a first pad 212 located on an end of a first arm 213 on a first side of the recess 210, and a second pad 214 located on an end of a second arm 215 on a second side of the recess 210. The recess 210 is sized to receive the inferior portion of the urethra. In one embodiment, the recess 210 is provided as a semicircular face 36 that is aligned on the central longitudinal axis A. The recess 210 has a curvature that is similar to (or complements) the curvature of the inferior side of the urethra. The recess 210 is adapted to immobilize the urethra and is provided with suction ports similar to the suction ports 50 described above.

The handle 204 is similar to the handle 28 described above and includes the connector 40 and the actuator coupled with the first switch 42 and the second switch 44.

FIG. 8 is a front end view of the head 202 of the tool 200. The suction ports 50 are illustrated aligned on a vertical longitudinal axis of the tool 200. Other configurations for the location of the suction ports 50 are also acceptable.

The first pad 212 is located on one side of the recess 210 opposite from the second pad 214. In one embodiment, the first pad 212 is provided with a first height H1 and a second pad is provided with a height H2 that is less than the first height H1. The first pad 212 is provided with an opening 260 through which the piercing mechanism 262 moves. The tool 200 allows the piercing mechanism 262 to move out of the first pad 212 to a superior exterior surface 270 that is exposed on top of the second pad 214. In this manner, the piercing mechanism 262 is available to be attached to the cuff 108 of the artificial sphincter (FIG. 6). For example, upon delivering the piercing mechanism 262 through the tissue behind the urethra, the surgeon has access to the piercing mechanism 262. Upon retraction of the piercing mechanism 262, the cuff is retracted through the channel that was formed in the tissue behind the urethra by the piercing mechanism 262.

FIG. 9A is a front end view and FIG. 9B is a lateral cross-sectional view of the tool 200. The piercing mechanism 262 is moved out of the opening 260 from the first pad 212 across the gap formed by the recess 210. The piercing mechanism 262 moves to the superior exterior surface 270 of the second pad 214. The piercing mechanism 262 becomes located above (on top of) the second pad 214 in an orientation that exposes the engagement device 280 for access by the surgeon. The engagement device 280 is positioned to receive the cuff of the artificial sphincter since the piercing mechanism 262 is exposed above the second pad 214. The surgeon attaches the cuff of the artificial sphincter to the engagement device 280 and retracts the piercing mechanism 262, which draws the cuff back through the tissue to place the artificial sphincter behind (superior) to the urethra. The engagement device 280 configures the tool as an all-in-one tool for forming a passage in tissue behind (superior) to the urethra and delivering the cuff of an artificial sphincter through the passage.

Figure 10A:
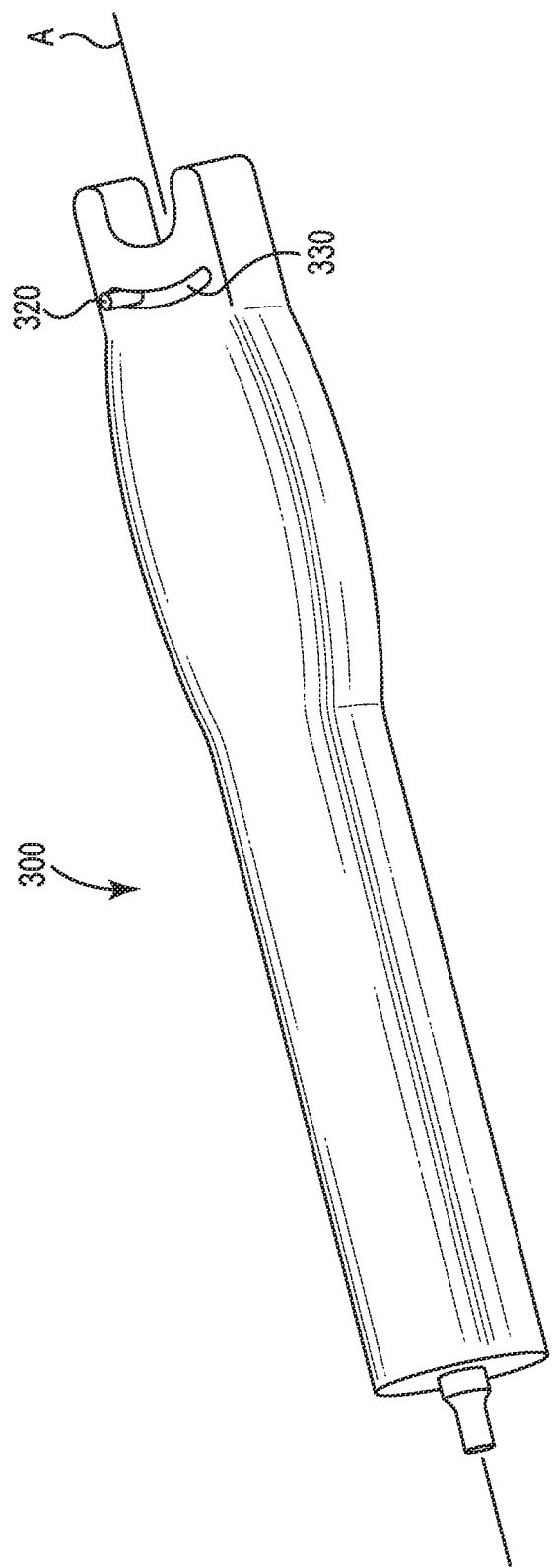
FIG. 10A is a perspective view of one embodiment of a surgical tool that is adapted for placement of a cuff of an artificial urinary sphincter around a portion of a urethra.
Figure 10B:
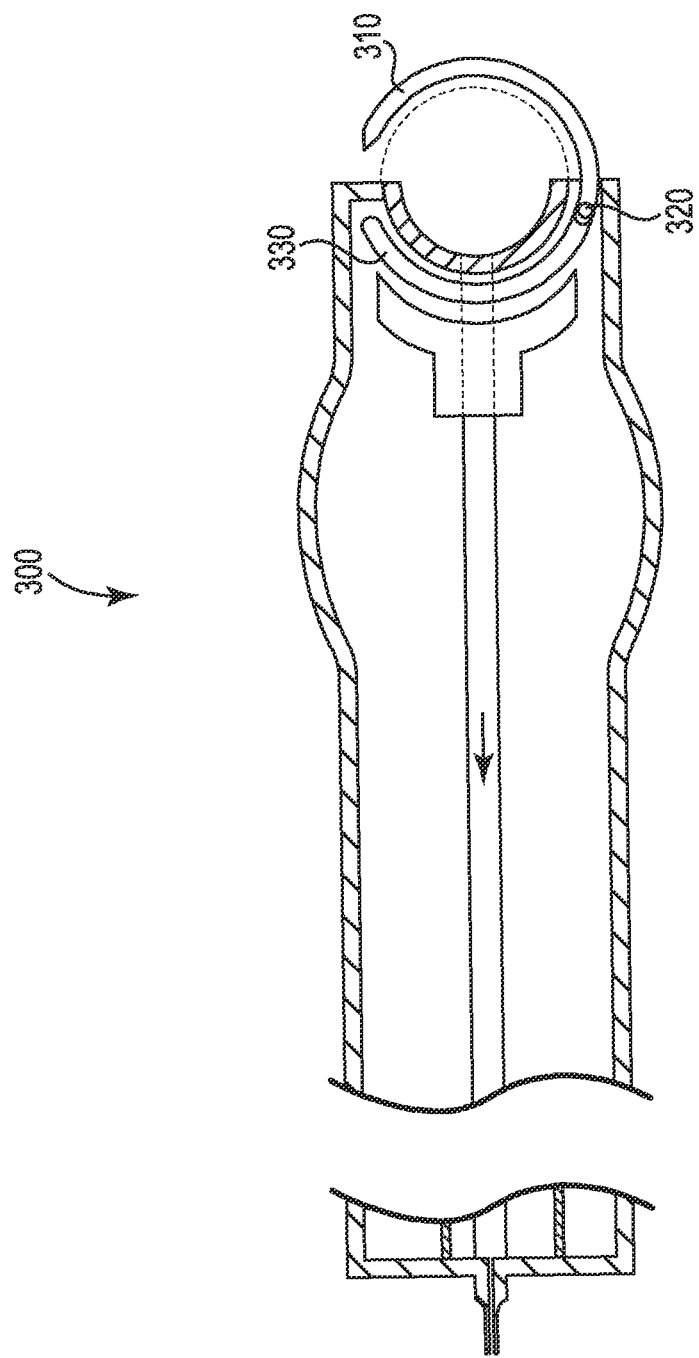
FIG. 10B is a cross-sectional view of the tool illustrated in FIG. 10A with a piercing blade deployed from the tool.

FIG. 10A is a perspective view and FIG. 10B is a cross-sectional view of one embodiment of a surgical tool 300 that is adapted for placement of a cuff of an artificial urinary sphincter around a portion of a urethra. The tool 300 is mechanically operated to deploy a piercing blade 310 in response to the movement of a blade slider 320. The blade slider 320 is acceptably provided as a knob, or a button, or a plunger, or a trigger. The blade slider 320 is directly coupled with the piercing blade 310 so that the blade 310 moves in direct 1:1 relationship with the slider 320. In one embodiment, the blade slider 320 is retained within a trace 330 such that the slider 320 sits in the trace 330 and is contained by the housing assembly/handle.

FIGS. 11-15 illustrate the use of the surgical system 30 and a method of dissecting tissue away from behind of or superior to the urethra.

Figure 12:
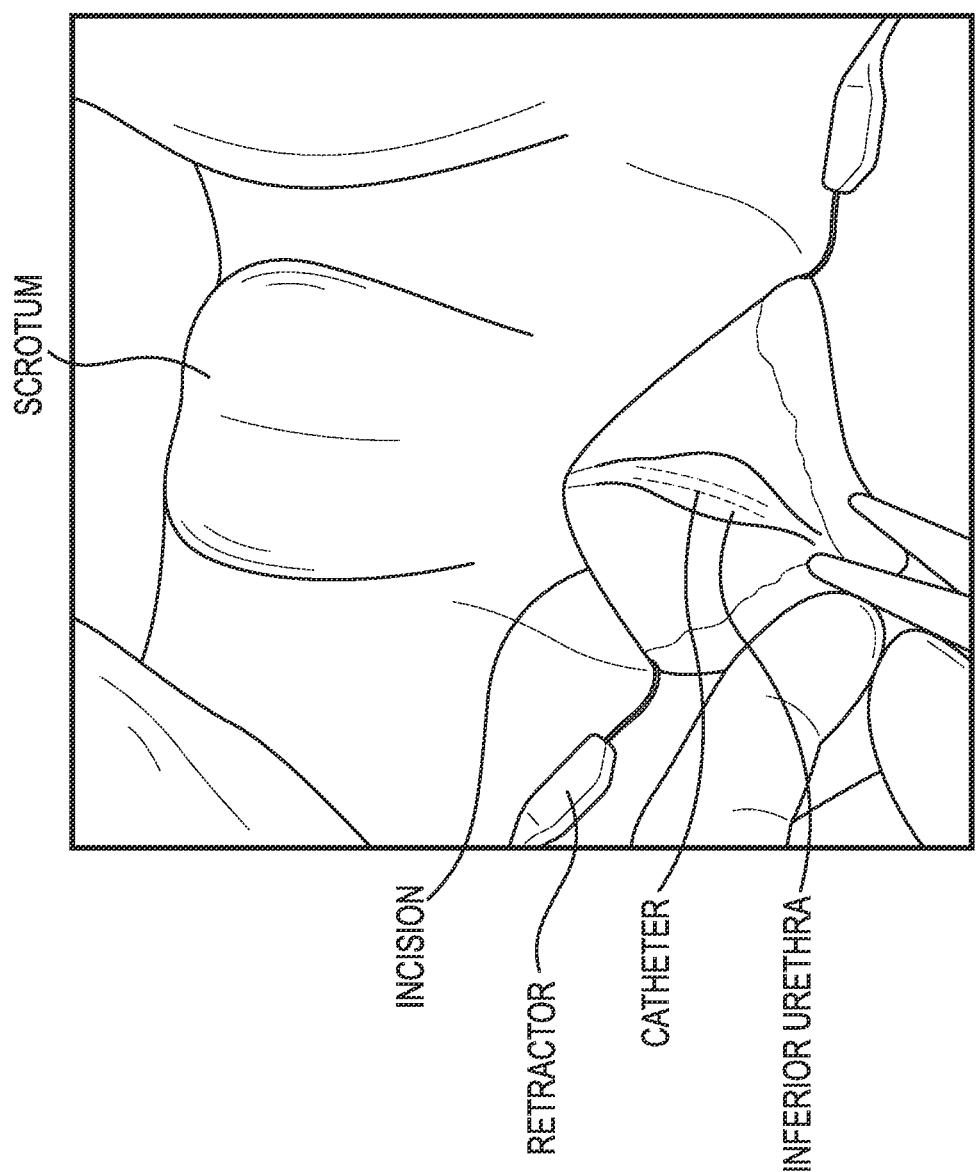

FIGS. 11-12 are a schematic views of a male patient prepped for surgery. The patient is in a lithotomy position with the knees elevated above the head. The scrotum is elevated cephalad. A catheter is inserted into the urethra to drain urine from the bladder and to provide the urethra with a firmness that can be palpated by the surgeon. The surgeon forms an incision in the perineum between the scrotum and the anus. An angled scissors or other device is employed to dissect tissue and tissue layers away from the inferior side of the bulbar urethra. The tissue is dissected inferior to the urethra to expose the front portion of the bulbar urethral complex. Tissue is dissected laterally relative to the incision as far as the surgeon is able to visual, leaving tissue connected to the superior side of the urethra. The fascia around the bulbospongiosus muscle has been dissected to expose a portion of the bulbar muscle and bulbar urethra for access by the surgeon.

Figure 13:
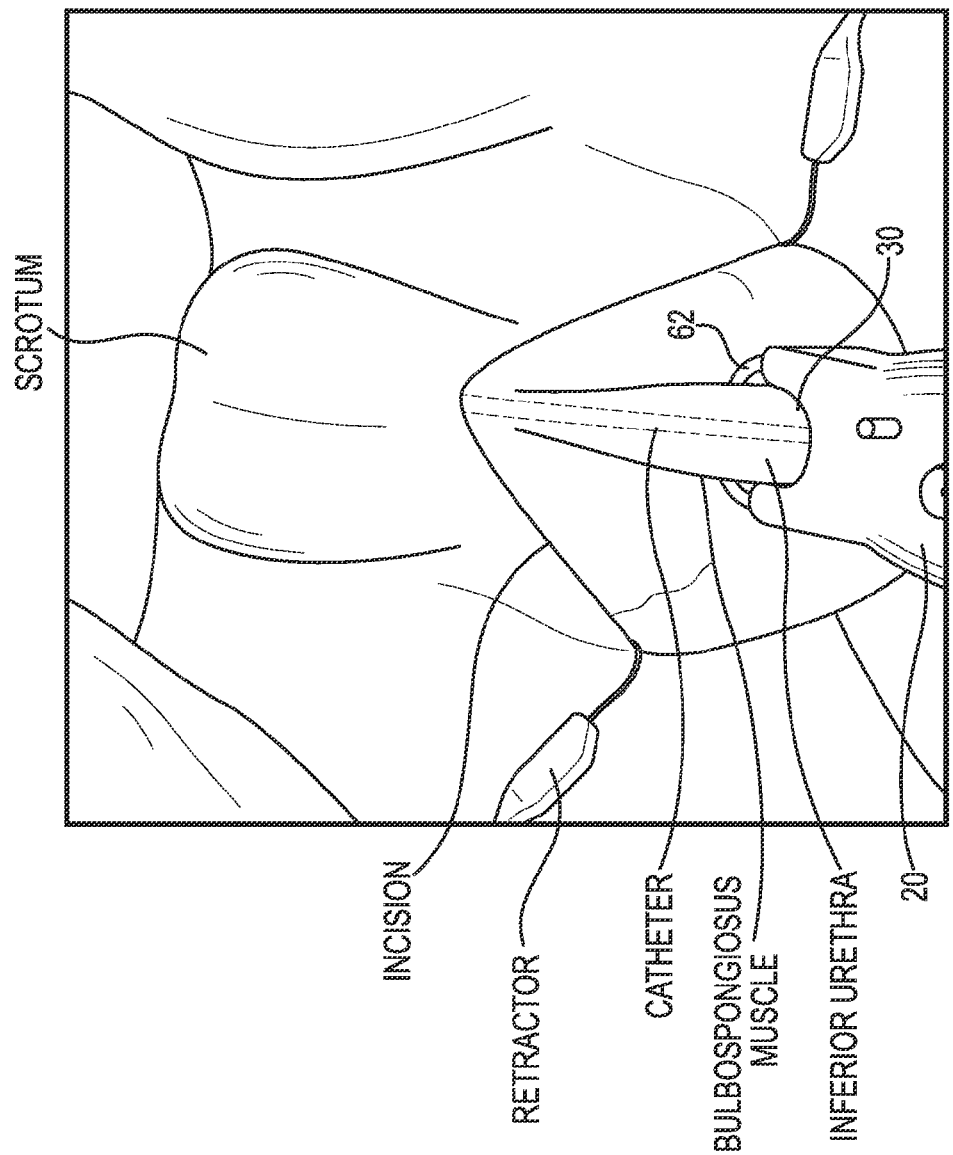

FIG. 13 is a schematic view of the urethra, and the bulbar muscle around the urethra, exposed within the incision. The inferior portion of the urethra is visible to the surgeon. The tool 20 is engaged on either side of the urethra and the urethra is immobilized, for example with the use of suction delivered to the recess 30. The piercing mechanism 62 is deployed to form a path superior to the urethra. As described above, the cuff 108 of the artificial sphincter can be attached to the piercing mechanism 62, and upon retraction of the piercing mechanism 62, the cuff 108 is pulled or drawn into position behind the urethra. Alternatively, the piercing mechanism 62 is retracted leaving a channel in the tissue superior to the urethra, and the cuff 108 is guided through the channel by the surgeon, for example through the use of a forceps of pushing tool. Another acceptable approach is for the surgeon to attach the cuff 108 to the piercing mechanism 62 prior to forming the path in the tissue superior to the urethra, and in this approach the cuff 108 is placed behind the urethra as the piercing mechanism 62 traverses through the tissue superior to the urethra.

Figure 15:
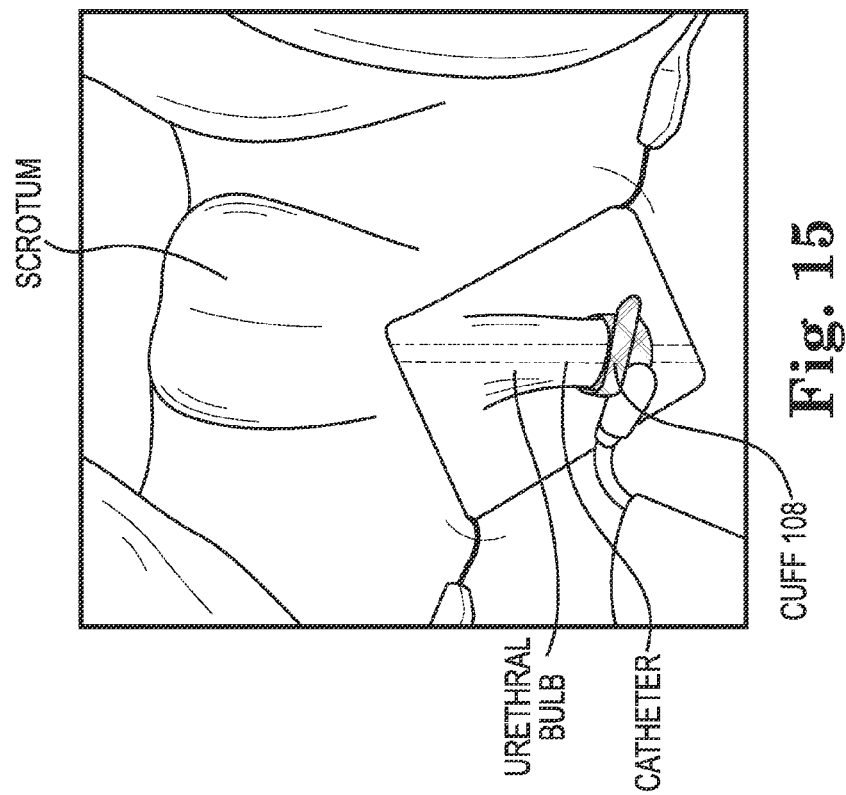
Figure 14:
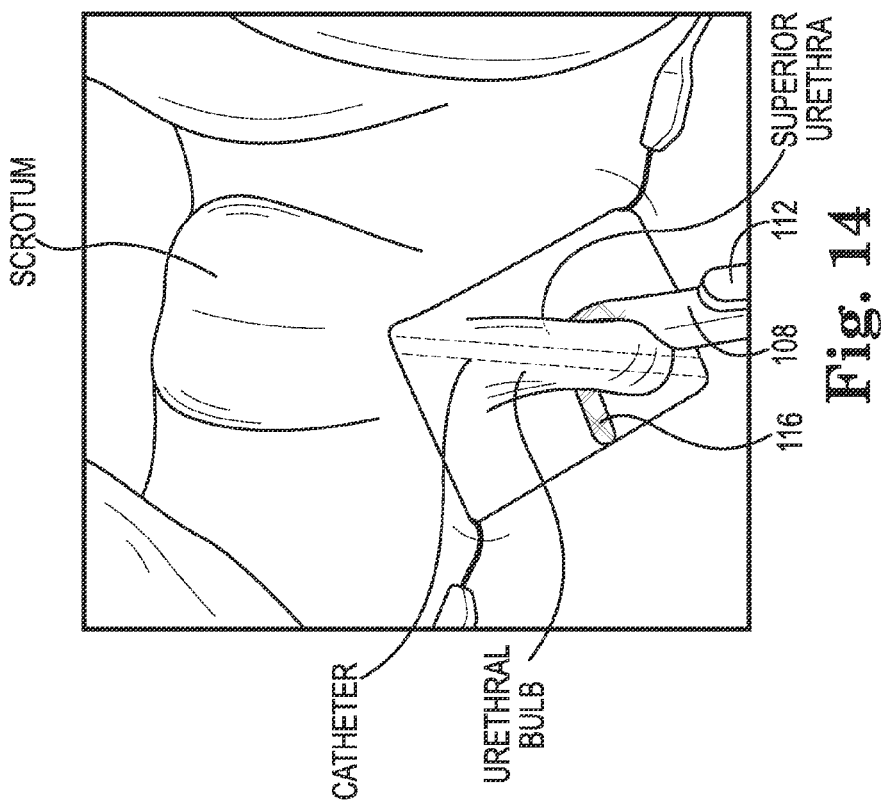

FIGS. 14-15 are schematic views illustrating the cuff 108 directed into a tissue channel formed behind the urethra by the tool 20. In FIG. 14, the attachment member 116 has been guided through the tissue channel behind the urethra. In FIG. 15, the cuff 108 has been secured around the urethra.

Embodiments provide a tool that allows the surgeon to dissect the tissue in front of the urethra with a scalpel while leaving the more difficult-to-see tissue connected superior to the urethra. The tools described above operate to form a channel in the tissue that is blocked from view of the surgeon by accommodating the urethra, immobilizing the urethra, and piercing the tissue in a safely calculated path behind the urethra. The artificial sphincter is directed through the channel. The use of the tools described above allows for dissecting tissue away from only the inferior urethra and leaving the tissue superior the urethra intact. The use of the tools described above allows for dissecting tissue away from the portion of the urethra that is oriented toward the surgeon, while leaving the difficult to see tissue behind the urethra intact.

Embodiments provide a tool that allows the surgeon to form a pathway behind a urethra useful for the placement of an artificial urinary sphincter around the urethra. Surgeons have communicated that dissecting tissue superior to the urethra presents a challenge when placing the cuff of an artificial urinary sphincter around the urethra. The tool described in this application provides a device and a method for dissecting tissue to form a pathway behind the urethra. The tools offers improved visualization of the placement of an artificial sphincter, improved repeatability of this procedure, automates this procedure, and reduces the steps of the procedure.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A surgical tool adapted for placement of a cuff of an artificial urinary sphincter around a portion of a urethra, the surgical tool comprising:
   a handle; and
   a head attached to the handle, the head comprising:
      a recess formed in a first end surface of the head, the recess sized to receive an inferior portion of the urethra and aligned with a central longitudinal axis of the handle;
      a first pad located on a first side of the recess;
      a second pad located on a second side of the recess and spaced a gap distance away from the first pad, with the first pad and the second pad located at a distal end of the tool;
      a piercing mechanism including a tip portion located in and movable out of one of the first pad and the second pad; and
      a suction port opening into the recess and configured to communicate with a suction source to allow the inferior portion of the urethra to be retracted into the recess; and
   wherein the piercing mechanism is movable across the gap distance between the first pad and the second pad to form a channel in tissue superior to the urethra, with the channel sized to receive the cuff of the artificial urinary sphincter;
   wherein the tip portion of the piercing mechanism includes an engagement device adapted to grasp an attachment member of the cuff of the artificial urinary sphincter;
   wherein the engagement device includes a slot that is sized to receive the attachment member, and a projection adapted to pierce through material of the attachment member, and
   wherein the handle includes an actuator that is connected to the piercing mechanism, wherein the actuator is configured to deploy the piercing mechanism and cause the tip portion and engagement device to move in a first direction between the first pad and the second pad, and to retract the piercing mechanism and cause the tip portion and engagement device to move in a second direction between the first pad and the second pad that is opposite the first direction.

2. The surgical tool of claim 1, wherein the recess is sized to immobilize the inferior portion of the urethra.

3. The surgical tool of claim 1, wherein the piercing mechanism is movable out of a first opening formed in the first pad and into a second opening formed in the second pad.

4. The surgical tool of claim 1, wherein the recess has a concave face in longitudinal cross-section that extends continuously between the first pad and the second pad.

5. The surgical tool of claim 4, wherein the recess includes a plurality of suction ports that are configured to communicate with a suction source to allow the concave face of the recess to retract the inferior portion of the urethra.

6. The surgical tool of claim 1, wherein a height of the first pad is greater than a height of the second pad.

7. The surgical tool of claim 6, wherein the piercing mechanism is retained in the first pad and is movable across the gap distance out from the first pad to a superior exterior surface of the second pad.

8. The surgical tool of claim 1, wherein a lateral cross-section of the piercing mechanism is arcuate in a shape of a semi-circle.

9. The surgical tool of claim 1, wherein the actuator is connected by a mechanical linkage to the piercing mechanism.

10. The surgical tool of claim 1, comprising one of a visual indicator and an aural indicator provided to indicate movement of the piercing mechanism.

11. A surgical tool adapted for placement of a cuff of an artificial urinary sphincter around a portion of a urethra, the surgical tool comprising:
 a handle;
 a head attached to the handle, the head comprising:
  a recess formed in a first end surface of the head, the recess sized to receive an inferior portion of the urethra and aligned with a central longitudinal axis of the handle;
  a first pad located on a first side of the recess;
  a second pad located on a second side of the recess and spaced a gap distance away from the first pad, with the first pad and the second pad located at a distal end of the tool;
  a piercing mechanism located in and movable out of one of the first pad and the second pad, the piercing mechanism having a proximal end tip portion; and
  a suction port opening into the recess and configured to communicate with a suction source to allow the inferior portion of the urethra to be retracted into the recess; and
 an actuator;
 wherein the piercing mechanism is movable across the gap distance between the first pad and the second pad to form a channel in tissue superior to the urethra, with the channel sized to receive the cuff of the artificial urinary sphincter;
 wherein the piercing mechanism incudes an engagement device adapted to grasp an attachment member of the cuff of the artificial urinary sphincter, with the engagement device located distal of on the proximal end tip portion;
 wherein the engagement device is a slot that is sized to receive the attachment member, with the slot defined by a continuous wall formed around an entire perimeter of the slot; and
 wherein the actuator is connected to the piercing mechanism and is configured to deploy the piercing mechanism and cause the tip portion and engagement device to move in a first direction between the first pad and the second pad, and to retract the piercing mechanism and cause the tip portion and engagement device to move in a second direction between the first pad and the second pad that is opposite the first direction.

12. The surgical tool of claim 11 wherein:
 the recess has a concave face in longitudinal cross-section; and
 the head comprises a plurality of suction ports opening into the recess and configured to communicate with a suction source to allow the inferior portion of the urethra to he retracted into the recess.

13. A surgical tool adapted for placement of a cuff of an artificial urinary sphincter around a portion of a urethra, the surgical tool comprising:
 a head comprising:
  a recess formed in a first end surface of the head, the recess sized to receive an inferior portion of the urethra;
  a first pad located on a first side of the recess;
  a second pad located on a second side of the recess and spaced a gap distance away from the first pad, with the first pad and the second pad located at a distal end of the tool;
  a piercing mechanism located in and movable out of one of the first pad and the second pad, the piercing mechanism having a proximal end tip portion; and
  a suction port opening into the recess and configured to communicate with a suction source to allow the inferior portion of the urethra to be retracted into the recess; and
 an actuator connected to the piercing mechanism; and
 wherein the piercing mechanism is movable across the gap distance between the first pad and the second pad to form a channel in tissue superior to the urethra, with the channel sized to receive the cuff of the artificial urinary sphincter;
 wherein the piercing mechanism includes a hole located on the proximal end tip portion, with the hole sized to receive an attachment member of the cuff of the artificial urinary sphincter, and the hole is defined by a continuous closed wall formed around an entire perimeter of the hole; and
 wherein the actuator is configured to deploy the piercing mechanism and cause the tip portion and hole to move in a first direction between the first pad and the second pad, and to retract the piercing mechanism and cause the tip portion and hole to move in a second direction between the first pad and the second pad that is opposite the first direction.

14. The surgical tool of claim 13 wherein:
 the recess has a concave face in longitudinal cross-section; and
 the head comprises a plurality of suction ports opening into the recess and configured to communicate with a suction source to allow the inferior portion of the urethra to be retracted into the recess.

* * * * *

UNITED STATES PATENT AND TRADEMARK OFFICE
CERTIFICATE OF CORRECTION

PATENT NO. : 9,877,817 B2
APPLICATION NO. : 14/284407
DATED : January 30, 2018
INVENTOR(S) : Geoffrey A. Daniel and Neal Poucher Page 1 of 1

It is certified that error appears in the above-identified patent and that said Letters Patent is hereby corrected as shown below:

In the Claims

Claim 12 at Column 12, Line 7:
"... urethra to he retracted into the recess" should read "... urethra to be retracted into the recess"

Signed and Sealed this
Twenty-fifth Day of December, 2018

Andrei Iancu
*Director of the United States Patent and Trademark Office*